United States Patent [19]

Sulkowski et al.

[11] 4,297,373
[45] Oct. 27, 1981

[54] METHOD OF SUPPRESSING CARDIAC ARRHYTHMIAS

[75] Inventors: Theodore S. Sulkowski, Wayne; James L. Bergey, Lansdale; Albert A. Mascitti, Norristown, all of Pa.

[73] Assignee: American Home Products Corporation, New York, N.Y.

[21] Appl. No.: 195,568

[22] Filed: Oct. 9, 1980

[51] Int. Cl.³ .................... A61K 31/17; C07C 127/00
[52] U.S. Cl. ..................................... 424/322; 564/48; 564/53
[58] Field of Search ......................................... 424/322

[56] References Cited

U.S. PATENT DOCUMENTS 2,762,842 9/1956 Hafliger et al. .................... 260/553
3,933,833 1/1976 Trepanier et al. ............. 424/322 X
4,224,242 9/1980 Sulkowski et al. ............. 424/322 X

FOREIGN PATENT DOCUMENTS 778647 2/1956 United Kingdom .

OTHER PUBLICATIONS

Koelzer et al., Arzneimittel–Forsch, 8, 664–671 (1958).
Dahlbom et al., Acta. Chem. Scan. 9, 1553 (1955).
Chiti, Il Pharmaco. Ed. Sc., XV, 114–125 (1960).
Beaver et al., J. Am. Chem. Soc., 79, 1236 (1957).
Wenker, J. Am. Chem. Soc., 60, 158 (1938).
Dovlatyan et al., Arm. Khim. Z. H. 19 (10) 774–777 (1966) USSR, also Chem. Abstr. 69, entry 32401f.

*Primary Examiner*—Frank Cacciapaglia, Jr.
*Attorney, Agent, or Firm*—Arthur G. Seifert

[57] ABSTRACT

Method of suppressing cardiac arrhythmias compounds of the formula:

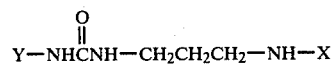

wherein:
Y is 2,6-dimethylphenyl, 2,5-dimethylphenyl, 5-bromo-2-methylphenyl, or 5-chloro-2-methylphenyl; and
X is propenyl, propynyl, or cyclopropyl; or a non-toxic, pharmaceutically acceptable acid addition salt thereof.

6 Claims, No Drawings

METHOD OF SUPPRESSING CARDIAC ARRHYTHMIAS

This invention relates to N-(3-(propenylaminopropyl)-N'-(disubstituted)phenylureas, N-(3-propynylaminopropyl)-N'-(disubstituted)phenylureas, or N-(3-cyclopropylaminopropyl)-N'-(disubstituted)-phenylureas which are useful in the treatment of cardiac arrhythmias. Heretofore the treatment of arrhythmias has been limited by drug toxicity, undesirable side-effects, or variable effectiveness. Accordingly, a great need exists for an anti-arrhythmic agent which is efficacious and less toxic and which has a lower incidence of undesirable side-effects than known anti-arrhythmic agents.

In particular, the invention comprises chemical compounds of the formula:

   I wherein:
Y is 2,6-dimethylphenyl, 2,5-dimethylphenyl, 5-bromo-2-methylphenyl, or 5-chloro-2-methylphenyl; and
X is propenyl, propynyl, or cyclopropyl;
or a non-toxic pharmaceutically acceptable acid addition salt thereof.

The compounds of Formula I wherein X is propenyl or propynyl are preferred. Also preferred are those compounds of Formula I wherein Y is 2,6-dimethylphenyl or 5-chloro-2-methylphenyl.

The compounds of Formula I exhibit cardiac antiarrhythmic activity as demonstrated in laboratory tests involving a variety of arrhythmic animal models. The compounds are therefore useful in treating both atrial and ventricular arrhythmias resulting from various underlying conditions, such as ischemic heart disease, myocardial infarction, congenital cardiac defects, digitalis overdose, myocarditis, or other pathological or toxic processes which may alter the electrical excitability of the heart.

The compounds of Formula I can be prepared by conventional synthetic methods. They are preferably prepared by a method in which a compound of the formula:

   II where W is a halogen, is reacted with an amine of the formula NH₂X, in which X and Y are as previously defined herein. The starting material (II) is prepared by reacting a disubstituted phenyl isocyanate with a halopropylamine of the formula H₂N-CH₂CH₂CH₂-W, where W is a halogen. These reactions should be carried out in an inert solvent, such as acetonitrile, chloroform, methylene chloride, or carbon tetrachloride.

A further method is by the reaction of an appropriate disubstituted phenyl isocyanate with an N-propenylamino-1,3-diaminopropane in an inert organic solvent, such as dichloromethane. [Note, "propenyl" may read "propynyl" or "cyclopropyl".] In order to optimize the yield, the reaction should be carried out with an excess of the diaminopropane and at a low temperature. A molar ratio of about 3 to 1 (diamine to isocyanate) is preferred and a temperature of about −5° to +5° C. is desirable.

In an alternative method, an appropriate disubstituted phenyl isocyanate is first reacted with an N-protected-N'-propenyl-1,3-diaminopropane in an inert solvent, (such as chloroform, dichloromethane, or benzene) to form the protected intermediate (III):

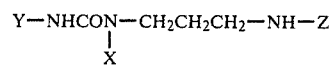   III wherein Y and X have the meanings hereinbefore defined and Z is a conventional protecting group for an amino group. The protecting group is then removed to afford the deprotected intermediate IV:

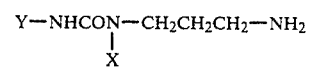   IV

If the deprotection step is performed under the influence of heat, the intermediate (IV) undergoes an intramolecular aminolysis of the amide in situ resulting in substitution of the propenyl group (X) at the terminal position of the chain. [Note, "propenyl" may read "propynyl" or "cyclopropyl" above also.] The initial reaction between the isocyanate and the protected diamine is carried out in an inert solvent, such as chloroform, dichloromethane, or benzene. If the deprotection reaction is carried out at room temperature, the deprotected intermediate IV can be isolated, and it can thereafter be converted to the final product by heating the intermediate in a suitable solvent, such as chloroform.

Protecting groups for an amino group are known in the art. Suitable groups are those which will prevent undesirable side reactions from occurring at the amino group during the initial reaction and which will be easily removed under mild conditions after the initial reaction.

Methods for making the protected amino compounds and for removing the protecting groups are well-known in the art. Preferred protecting groups are the carbobenzoxy group and the anisylidene group. The anisylidene group can be removed by treating the protected amine intermediate with hydroxylamine p-toluene-sulfonate in refluxing dioxane or ethyl alcohol. Under such conditions aminolysis takes place in situ. The carbobenzoxy group can be removed by treatment with hydrogen bromide in acetic acid at room temperature. The deprotected amine (IV) can be isolated and thereafter converted to the final product by mild heating.

The compounds of Formula I can be isolated in the form of the free base or in the form of a non-toxic acid addition salt prepared by reaction of the free base with a pharmaceutically acceptable organic or inorganic acid. Suitable acids will be apparent to those skilled in the art. Examples of such acids are p-toluene sulfonic (tosyl), hydrochloric, or phosphoric. The tosyl and hydrochloric salts are generally preferred.

In another aspect, the invention provides a method of suppressing cardiac arrhythmias in warm-blooded animals which comprises administering to said animal orally or parenterally an effective amount of a compound of Formula I, wherein X and Y are as hereinabove defined, or a non-toxic, pharmaceutically acceptable acid addition salt thereof. The anti-arrhythmic dosage of a compound of Formula I will vary according to the particular subject being treated, the severity and nature of the arrhythmia, and the particular subject being treated. Therapy should be initiated at a low dosage thereafter being increased until the desired anti-arrhythmic effect is obtained. In general, with large warm-blooded animals (about 70 kg. body weight) effective results can be achieved by the oral route at a daily dosage level of about 5–30 mg/kg. of body weight given as needed.

In yet another aspect, the invention provides a pharmaceutical composition comprising: (a) a compound of Formula I, wherein X and Y have the meanings hereinbefore defined, or a nontoxic, pharmaceutically acceptable acid addition salt thereof, and (b) a pharmaceutically acceptable carrier.

The active substances may be administered alone or in combination with pharmaceutically acceptable carriers, the proportion and nature of which are determined by the solubility and chemical properties of the compound selected, the chosen route of administration, and standard pharmaceutical practice. For example, the compounds of Formula I may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance: lactose, sucrose, magnesium stearate, resins, and like materials. Liquid oral forms may contain various flavoring, coloring, preserving, stabilizing, solubilizing, or suspending agents. Parenteral preparations are sterile aqueous or non-aqueous solutions or suspensions which may contain various preserving, stabilizing, buffering, solubilizing, or suspending agents. If desired, additives, such as saline or glucose may be added to make the solutions isotonic.

The suppression of arrhythmias by the compounds of Formula I can be elicited and demonstrated in the test procedures described below.

In each test, dogs of both sexes are anesthetized by administration of sodium pentobarbital injected I.V. at a dose of 35 mg/kg. Positive pressure artificial respiration with room air is utilized. Blood pressure is recorded from a femoral artery by means of a pressure transducer and oscillograph.

A. Suppression of electrical-stimulated ventricular fibrillations (fibrillatory threshold). The "fibrillatory threshold" is the voltage at which ventricular fibrillation is produced by an external electrical stimuli delivered to the left ventrical during the repolarization phase of the myocardium. In this test, the anti-arrhythmic activity of a compound is assessed by its ability to increase the fibrillatory threshold in anesthetized dogs.

Ventricular fibrillation is produced in an anesthetized dog by stimulating the left ventricular epicardium for periods of 5 seconds with pulses of 3 msec. duration at a frequency of 60 Hz. The stimuli are applied through bipolar platinum electrodes, 3.5 mm. apart, embedded in plastic plaque measuring 7×12 mm. which is sutured to the epicardium. The train of stimuli is triggered by the R-wave of the electrocardiogram and applied at increasing intensities (voltages) at 1 min. intervals until fibrillation occurs. The animal is defibrillated by a DC countershock and the sequence resumed after 10 min. Test drug is injected I.V. over a period of 5–10 min. Fibrillation threshold is determined before and starting at 10 min. after injection of each dose of drug. An increase in threshold of less than +0.75 volts is considered inactive; +0.75–0.99 volts is considered borderline; +1.0–1.24 volts is considered slight; +1.25–1.99 volts is considered moderate; and +2.0 volts or more is considered marked.

When tested by the procedure set forth above, the compounds described in Examples 1, 2 and 3 produced a slight to marked increase in fibrillatory threshold at a dose of 10–20 mg/kg., as shown in Table I below. (In this specification, unless indicated otherwise, the compounds were tested in the acid addition salt form obtained in the preparation example for that compound).

TABLE I

| Compound | Increase in Threshold (Volts) | |
|---|---|---|
| | 10 mg/kg. | 20 mg/kg. |
| 1 | 1.6 ± 0.3 | 3.4 ± 0.4 |
| 2 | 1.1 ± 0.3 | 2.2 ± 0.4 |
| 3 | 0.8 ± 0.4 | 1.0 ± 0.6 |

B. Suppression of ventricular arrhythmias produced by ouabain. The I.V. injection of ouabain results in ventricular arrhythmias. In this test, the anti-arrhythmic activity of a compound is assessed by its ability to restore normal sinus rhythm in ouabain-treated, pentobarbital anesthetized dogs. Ouabain is injected I.V. to an anesthetized dog in an initial dose of 50 $\mu$g/kg. and then in incremental doses until a ventricular arrhythmia (multiform ventricular beats or ventricular tachycardia) is produced. A total dose of 55 to 60 $\mu$g/kg. is usually sufficient to produce the arrhythmia. The test compound is then injected I.V. over approximately 3–5 min., starting 20 min. after the injection of ouabain, and the effect on the arrhythmia is observed. Drug injection is terminated when reversion to sinus rhythm is observed. In untreated dogs, the arrhythmia persists greater than 45 minutes.

C. Suppression of ventricular arrhythmias produced by coronary ligation. Ligation of the left anterior descending coronary artery in two stages over a 20 minute period results in severe ventricular arrhythmias beginning at 5–7 hours and lasting about 48 hours. By the third day, arrhythmias spontaneously subside and normal rhythm is reestablished. The severity of the arrhythmia is greatest within 24 hours following ligation. In this test, the anti-arrhythmic activity of a test compound is assessed by the ability of the compound to restore normal sinus rhythm in the coronary ligated dog. The left anterior descending coronary artery of an anesthetized dog is ligated in two stages at the level of the atrial appendage. The animals recover from anesthesia and the test compound is administered to the conscious dog by I.V. injection or orally (via gastric tube) at 18 to 24 hours after ligation. The test compound is administered until reversion of sinus rhythm occurs or until the intended dose is given.

EXAMPLE 1

N-(2,6-Dimethylphenyl)-N'-[3-(2-Propenylamino)-Propyl]Urea

A mixture of 72 grams of N-(3-chloropropyl)-N'-(2,6-dimethylphenyl)urea, 300 ml. of acetonitrile and 50 grams of allylamine was heated at reflux for 18 hours. The solution was evaporated to dryness in vacuo and the residue was partitioned between water and dichloromethane. The dichloromethane was extracted with 250 ml. of 20% hydrochloric acid (V/V). The acid extract was cooled in an ice bath and made basic with saturated sodium carbonate solution. The mixture was extracted with dichloromethane. The extract was dried over magnesium sulfate, then evaporated to dryness. The residue was triturated with ether to obtain a solid, m.p. 107°–110° C.

The solid was treated with p-toluenesulfonic acid to obtain the salt. Two recrystallizations from ethanol-ether afforded N-(2,6-dimethylphenyl)-N'-[3-(2-propenylamino)propyl]urea, 4-methylbenzenesulfonate, m.p. 111°–113° C.

Analysis for: $C_{15}H_{23}N_3O.C_7H_7SO_3H$ (433.56); Calculated: C, 60.94; H, 7.21; N, 9.69; S, 7.40. Found: C, 60.68; H, 6.88; N, 9.58; S, 7.65.

EXAMPLE 2

N-(2,6-Dimethylphenyl)-N'-[3-(2-Propynylamino)-Propyl]Urea

A mixture of 65 grams of N-(3-chloropropyl)-N'-(2,6-dimethylphenyl)urea, 350 ml. of acetonitrile, and 50 grams of propargylamine was refluxed for 19 hours. The reaction mixture was filtered and the filtrate was evaporated to dryness in vacuo. The residue was dissolved in chloroform and extracted with 250 ml. of 20% hydrochloric acid. The acid extract was cooled and made basic with 50% sodium hydroxide solution. The mixture was extracted with dichloromethane. After drying over magnesium sulfate, the dichloromethane was removed in vacuo to obtain a solid residue, m.p. 139°–143° C. The solid was treated with p-toluenesulfonic acid to obtain the salt. Recrystallization from ethanol-ether afforded N-(2,6-dimethylphenyl)-N'-[3-(2-propynylamino)propyl]urea, 4-methylbenzenesulfonate, m.p. 143°–144.5° C.

Analysis for: $C_{15}H_{21}N_3O.C_7H_7SO_3$ (431.54); Calculated: C, 61.28; H, 6.77; N, 9.74; S, 7.43. Found: C, 60.96; H, 6.83; N, 9.97; S, 7.47.

EXAMPLE 3

N-[3-(Cyclopropylamino)Propyl]-N'-(2,6-Dimethylphenyl)Urea

A mixture of 70 grams of N-(3-chloropropyl)-N'-(2,6-dimethylphenyl)urea, 350 ml. of acetonitrile and 50 grams of cyclopropylamine was refluxed for 18 hours. The acetonitrile was evaporated in vacuo. The residue was dissolved in dichloromethane and shaken with saturated sodium carbonate solution. The dichloromethane portion was extracted twice with 250 ml. of water, then extracted with 250 ml. of 20% hydrochloric acid. The acid solution was cooled and made basic with 50% sodium hydroxide solution. The mixture was extracted with dichloromethane. The extract was dried over magnesium sulfate, then evaporated to dryness in vacuo. The residue was triturated with hot ether and the solid was separated by filtration. The solid was treated with p-toluenesulfonic acid to obtain the salt. Two recrystallizations from ethanol-ether afforded N-[3-(cyclopropylamino)propyl]-N[-(2,6-dimethylphenyl)urea], 4-methylbenzenesulfonate], m.p. 124°–126° C.

Analysis for: $C_{15}H_{23}N_3O.C_7H_7SO_3H$ (433.56); Calculated: C, 60.94; H, 7.21; N, 9.69; S, 7.40. Found: C, 60.82; H, 7.35; N, 9.48; S, 7.63.

What is claimed is:

1. A method of suppressing cardiac arrhythmias in warm-blooded animals comprising administering to an animal in need thereof an amount effective to suppress such arrhythmia of a compound of the formula:

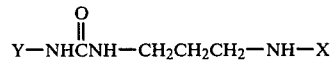

wherein:

Y is 2,6-dimethylphenyl, 2,5-dimethylphenyl, 5-bromo-2-methylphenyl, or 5-chloro-2-methylphenyl; and X is propenyl, propynyl, or cyclopropyl;

or a non-toxic, pharmaceutically acceptable acid addition salt thereof.

2. The method of claim 1 in which X is propenyl or propynyl.

3. The method of claim 1 in which the compound is N-(3-propenylaminopropyl)-N'-(2,6-dimethylphenyl)urea.

4. The method of claim 1 in which the compound is N-(3-propynylaminopropyl)-N'-(2,6-dimethylphenyl)urea.

5. The method of claim 1 in which the compound is N-(3-cyclopropylaminopropyl)-N'-(2,6-dimethylphenyl)urea.

6. The method of claim 1 in which the non-toxic, pharmaceutically acceptable acid addition salt is 4-methylbenzenesulfonate.

* * * * *